United States Patent
Bailly et al.

(10) Patent No.: US 6,779,701 B2
(45) Date of Patent: Aug. 24, 2004

(54) APPLIANCE FOR STORING, DISTRIBUTING AND PLACING COUCHED I-SHAPED SURGICAL FASTENERS

(75) Inventors: Pierre Bailly, Caluire (FR); Frederic Evrard, Limas (FR); Michel Therin, Lyons (FR); Salomon Benchetrit, Caluire (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 10/376,588

(22) Filed: Mar. 3, 2003

(65) Prior Publication Data
US 2003/0187465 A1 Oct. 2, 2003

(30) Foreign Application Priority Data
Mar. 8, 2002 (FR) .............................. 02 03082

(51) Int. Cl.⁷ .............................................. A61B 17/04
(52) U.S. Cl. ..................... 227/176.1; 227/67; 227/19
(58) Field of Search .................. 227/67, 68, 176.1, 227/19; 604/57, 60, 61, 62, 63, 64, 139

(56) References Cited

U.S. PATENT DOCUMENTS

| | | | |
|---|---|---|---|
| 3,399,432 A | | 9/1968 | Merser |
| 3,716,058 A | | 2/1973 | Tanner, Jr. |
| 3,875,648 A | | 4/1975 | Bone |
| 3,995,581 A | | 12/1976 | Smejda |
| 4,039,078 A | * | 8/1977 | Bone .......................... 206/343 |
| 4,049,177 A | * | 9/1977 | Bussard ....................... 227/67 |
| 4,111,347 A | | 9/1978 | Bone |
| 4,121,487 A | | 10/1978 | Bone |
| 4,448,194 A | | 5/1984 | DiGiovanni et al. |
| 4,533,076 A | * | 8/1985 | Bourque ....................... 227/67 |
| 4,657,461 A | | 4/1987 | Smith |
| 4,669,473 A | | 6/1987 | Richards et al. |
| 4,681,248 A | * | 7/1987 | Duchin ......................... 227/73 |
| 4,696,300 A | | 9/1987 | Anderson |
| 4,736,746 A | | 4/1988 | Anderson |
| 5,024,365 A | * | 6/1991 | Bourque ....................... 227/67 |
| 5,203,864 A | | 4/1993 | Phillips |
| 5,290,296 A | | 3/1994 | Phillips |
| 5,320,633 A | | 6/1994 | Allen et al. |
| RE34,857 E | | 2/1995 | Kunreuther |
| 5,470,337 A | | 11/1995 | Moss |
| 5,482,196 A | * | 1/1996 | Doyel .......................... 227/67 |
| 5,601,571 A | | 2/1997 | Moss |
| 5,615,816 A | * | 4/1997 | Deschenes et al. ........... 227/71 |
| 5,755,371 A | | 5/1998 | Huang |
| 5,810,238 A | * | 9/1998 | Kunreuther .................. 227/71 |
| 5,810,848 A | | 9/1998 | Hayhurst |
| 5,997,552 A | | 12/1999 | Person et al. |
| 6,071,292 A | | 6/2000 | Makower |
| 6,152,935 A | | 11/2000 | Kammerer et al. |
| 6,206,895 B1 | | 3/2001 | Levinson |
| 6,245,080 B1 | | 6/2001 | Levinson |
| 6,319,263 B1 | | 11/2001 | Levinson |
| 6,398,796 B2 | | 6/2002 | Levinson |
| 6,425,900 B1 | | 7/2002 | Knodel et al. |
| 6,491,707 B2 | | 12/2002 | Makower et al. |
| 2001/0010005 A1 | | 7/2001 | Kammerer et al. |
| 2001/0044638 A1 | | 11/2001 | Levinson et al. |
| 2001/0044639 A1 | | 11/2001 | Levinson |
| 2002/0087170 A1 | | 7/2002 | Kuhns et al. |

FOREIGN PATENT DOCUMENTS

| | | |
|---|---|---|
| WO | WO 87/01270 | 3/1987 |
| WO | WO 98/51179 | 11/1998 |
| WO | WO 99/39645 | 8/1999 |
| WO | WO 00 67644 A | 11/2000 |

* cited by examiner

*Primary Examiner*—Scott A. Smith
*Assistant Examiner*—Chukwurah Nathaniel
(74) *Attorney, Agent, or Firm*—Oliff & Berridge, PLC (57) ABSTRACT

This appliance comprises, in a tubular body (20), a magazine slide (22) secured to a needle (50) and the magazine slide (22) containing fasteners (A), an element for distributing the fasteners one by one, and an ejection plunger (42) able to push the anchoring bar (2) of the awaiting first fastener (A) into the needle.

According to the invention, the magazine slide (22) comprises below the needle (50) a transverse finger (59) able, as the fastener is distributed by movement of its anchoring bar (2) by the plunger (42), to have the downstream end (3a) of this catching bar bear against it to force it to pivot by raising its upstream end (3b), beside the needle (50), a downwardly projecting rib (51) able to guide the pivoting of the upstream end (3b) of the catching bar (3) so that the latter does not butt against the needle, and, on the transverse finger (59), a sloping face (59a) driving the downstream end (3a) of the catching bar (3) transversely away from this finger.

9 Claims, 6 Drawing Sheets

APPLIANCE FOR STORING, DISTRIBUTING AND PLACING COUCHED I-SHAPED SURGICAL FASTENERS

BACKGROUND OF THE INVENTION

1. Field of Invention

The invention relates to an appliance for distributing and placing I-shaped surgical fasteners which may, for example, be used for fixing parietal and visceral reinforcements.

It is aimed more especially at replacing permanent metal fasteners and staples with fasteners made of plastic, for example, of resorbable material, having a temporary function consistent with the reinforcing tissue recovery time, while at the same time affording anchorage excluding the risks of trapping nerves.

2. Description of Related Art

Already known from the textile industry is a plastic fastener in the overall shape of an I, that is to say made up of a head, of a connecting filament and of a foot. This fastener is distributed and placed by means of an appliance in the form of a gun the barrel of which is extended by a hollow needle and the body of which is fitted with a manual actuating control. To connect various elements in sheet form, for example for connecting a label to a garment, the needle is engaged transversely through these elements, by pushing it in by hand, then actuation of the manual control, through the displacement of a plunger arranged along the longitudinal axis of the canal of the needle, causes:

- a fastener forming part of a strip of fasteners in attendance in a magazine to be selected,
- the head of the fastener to be moved into the axial canal of the hollow needle,
- the head of the fastener travelling along the needle to pass through the sheets,
- and then, as soon as the connecting filament comes into contact with the sheets, it to be folded down against the head and engage through the sheets with the remainder of the head until the head lies completely on the other side of the sheets that are to be held together.

At the end of actuation, a means, for example a spring, returns the plunger and the needle is withdrawn by hand. Under the action of the elasticity of the material of which the fastener is made, the head thereof returns to its initial position and once again becomes more or less perpendicular to the connecting filament, anchoring the fastener on the rear face of the sheets. These are then trapped between the head and the foot of the fastener which also runs transversely, but on the front side of the sheets.

It has been imagined for this type of fastener to be carried over into surgical ligatures, for example for binding a textile reinforcement against biological tissues, by making the fastener out of plastic and, in particular, out of a bioabsorbable material and by distributing it using an equivalent distributor. Disadvantages have then arisen and these stem from the bulk generated by the strip of fasteners projecting from the tip of the distributor, and from those inherent in meeting surgical specifications, particularly those relating to sterilization. This is the case of the appliances described in U.S. Pat. No. 4,448,194 and WO98/51179.

To overcome these disadvantages, document WO00/67644 describes a distribution and placement appliance comprising a handgrip body quipped with first and second controls and with an end-piece, and an elongate element, attached and fixed to the end-piece, in which appliance the elongate element is made up of a body of tubular overall shape containing:

- near its free end, a magazine slide itself containing couched I-shaped fasteners each having an anchoring bar, a catching bar and a connecting strip, the said slide being, on the one hand, movable in the elongate element by a longitudinal rod which can be actuated by the first controls on the handgrip and, on the other hand, secured to a split and longitudinal hollow needle projecting from its free end and able to project from this elongate element,
- and, in its tubular body, on the one hand, means for distributing the stored fasteners one by one, this distribution involving the transferring of the anchoring bar of the first fastener into an accommodating housing arranged in the continuation of the hollow needle and, on the other hand, an ejection plunger which can be moved by the second controls on the handgrip and which is arranged in line with the hollow needle so as to push the anchoring bar of the awaiting first fastener thereinto.

SUMMARY OF THE INVENTION

In this appliance, the fasteners are, in their storage magazine, subjected to the constant force of a pushing blade which urges them towards the free end of the appliance and which, in conjunction with a sloping ramp, tends to drive the anchoring bar of the first fastener into an accommodating housing formed behind the split needle, but closed off at rest by the plunger. Actuation of the controls on the handgrip first of all causes the slide to move so that the needle projects from the free end of the elongate element, this movement taking place with no movement of the plunger, so as to form the accommodating housing which then accommodates the anchoring bar of the first fastener.

Secondly, the plunger is moved by the second controls so as to drive the anchoring bar of the fastener into the needle, then from the needle into the biological tissues that are to take it. At the end of distribution, the catching bar of the fastener in the process of being placed passes against an inclined ramp belonging to the slide and which is supposed to cause it to pivot so that it does not come into abutment against the tissues but lies against them.

It has been found in practice that this ramp is not enough to cause the catching bar to pivot satisfactorily, which means that it can still butt against the reinforcement, impeding distribution and the righting movement that the anchoring bar needs to effect in the biological tissues.

It should be pointed out here that, unlike fasteners used for connecting textile components, in which the anchoring bar rights itself behind the sheets, but in the atmosphere, in order through the elasticity of the material of which it is made to adopt a position parallel to the sheets, the anchoring bar of a surgical fastener has to right itself in the biological tissues, that is to say against the resistance thereof. This righting entails a force that exceeds the elastic capabilities of the material and is not well catered for in the appliances of the prior art, which means that the positioning of the anchoring bar and the anchoring of the fastener in the biological tissues are haphazard.

These disadvantages are exacerbated with fasteners made of a material which has low elasticity or nervosity, as is the case of bioabsorbable materials because as the fastener is distributed into the tissues, the mechanical properties of the material reduce the elastic righting ability of its anchoring and catching bars, and this leads to poor anchorage in the tissues.

Finally, with fasteners made of bioabsorbable material or material with low elasticity, the constant pressure on them from the spring means pushing them towards the exit from the magazine tends to deform them in creep. This generates distribution problems leading to the scrapping of the appliance.

It is an object of the present invention to provide an appliance for storing, distributing and placing surgical fasteners which reduces the stresses exerted on the fasteners in attendance in the magazine and which makes them easier to place by organizing the movements that distribute them.

This appliance reuses the essential elements of the one described in document WO00/67644 described hereinabove, but reconfigures them.

To this end, the accommodating housing of the magazine slide contains, at rest, the anchoring bar of the first fastener awaiting placement, of which fastener the catching bar, arranged at the end of the magazine, is free of any thrusting force, while this magazine slide comprises:

below the needle and in the path via which the said catching bar leaves the magazine, a transverse finger able, as the fastener is distributed by movement of its anchoring bar by means of the plunger, to have the downstream end of this catching bar bear against it to force it to pivot by raising its upstream end, beside the needle, a downwardly projecting rib able to guide the pivoting and movement of the upstream end of the catching bar so that the latter does not butt against the needle, and, on the transverse finger, a sloping face driving the downstream end of the catching bar transversely away from this finger.

Thus, when the appliance is at rest, the first fastener and the next ones are not subjected to any thrusting force, including the first fastener the anchoring bar of which is already in place in the accommodating housing of the magazine slide. By virtue of this, the stored fasteners are kept in their original condition and are therefore not at risk from creep, even in the case of weakly elastic materials.

When the fastener is distributed, the finger, the rib and the slopes of the slide, which in turn collaborate with the catching bar, first of all allow the movement imparted by the plunger to the anchoring bar to be used to cause the catching bar to pivot and to orientate it roughly parallel to the reinforcement and then allow the catching bar to be used to retain the anchoring bar and force it to pivot in the biological tissues so that it adopts a position parallel to this textile reinforcement.

Thus, at the end of placement and without excessive stresses having been exerted on the fastener, the fastener is always perfectly positioned and therefore provides perfect anchoring.

In one embodiment of the invention, the catching bar of the first fastener is, in the magazine, in contact with the catching bars of the other fasteners stored, and the catching bar of the last fastener is in contact, but without significant force, with the end of a buffer rod which can be moved step by step, this buffer rod being connected to means able, at the end of the movement of distributing the first fastener into the tissues, and through movement of the second controls on the handgrip, to move it by the length of the catching bar of one fastener so that, as the magazine slide returns to its starting and rest position in the tubular body, contact between the end of this buffer rod and the catching bar of the last fastener causes the row of fasteners to move within the magazine, and causes the anchoring bar of the first fastener to be transferred into the accommodating housing.

Thus, once the first fastener has been distributed, the accommodating housing is reloaded automatically, as the slide returns into the body, by abutment of the catching bar of the last fastener against the buffer rod, which is moved forward by just one step corresponding to the length of the catching bar of a fastener.

Advantageously, the magazine slide is formed of two plastic shells joined together along their median, longitudinal and vertical plane, the shell secured to the hollow and split needle having two longitudinal slots arranged near its edges and able, one of them, to receive the catching bars of the fasteners and the other the anchoring bars, the slot for the catching bars opening freely at the front end of the slide while the slot for the anchoring bars continues in an inclined plane for guidance in the direction of the needle, while the other shell has a longitudinal channel coaxial with the needle for the ejection plunger and, in the accommodating housing of the needle, a vertically inclined resting plane for the connecting strip of a fastener.

Other features and advantages will become evident from the description which follows in reference to the appended schematic drawing which depicts one embodiment of the appliance according to the invention.

DETAILED DESCRIPTION OF PREFERRED EMBODIMENTS

Figures 1, 2, 3:
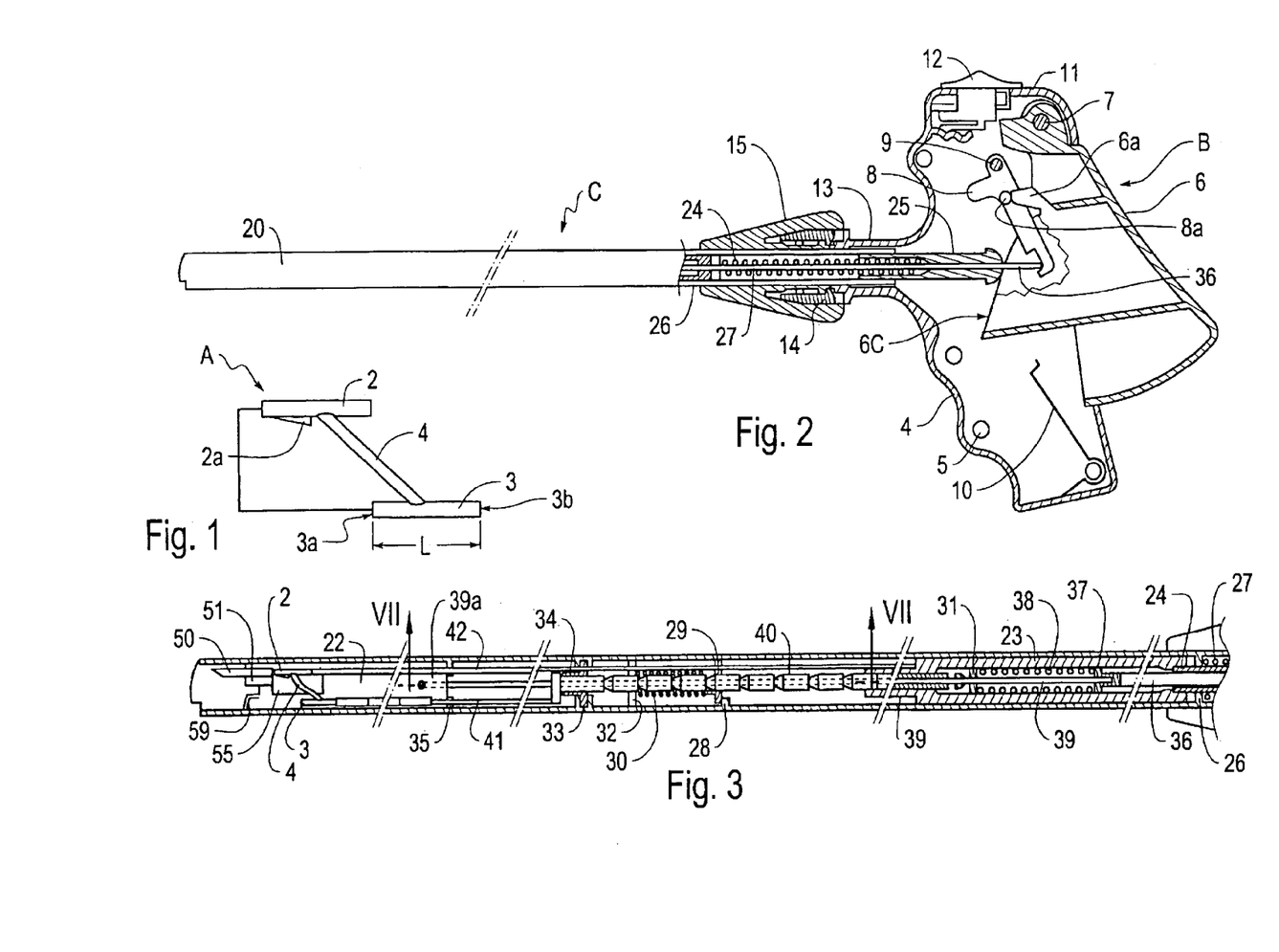
FIG. 1 is a side elevation of a fastener.
FIG. 2 is a general arrangement of the appliance, partly in elevation and partly in section through its handgrip and of the means of connection of this handgrip to the elongate body.
FIG. 3 is a part view in longitudinal section of the elongate element depicted on a larger scale by comparison with FIG. 2.

The appliance is intended to distribute staples A which, as shown in FIG. 1, have the overall shape of a couched I made up of two parallel bars, namely an anchoring bar 2 and a catching bar 3, which are connected by an inclined connecting strip 4. The anchoring bar 2 has a tooth 2a projecting from its part which is engaged first into human tissue. This fastener is made of plastic, particularly of biocompatible material, preferably of bioabsorbable material, but which may also not be bioabsorbable.

The appliance in itself is made up of two elements, namely an assembly B for holding and an elongate element C.

The element B for holding comprises a handgrip body 4, made in two symmetric parts assembled by ultrasonic welding or by rivets or screws 5, a handgrip 6 articulated on a transverse axle 7 of the body, a control lever 8 the upper end of which is articulated on a transverse axle 9 of the body, a torsion spring 11 arranged around the axle 7 and returning the handgrip 6 towards the outside of the body, a latch 12 mounted to slide in the body and able to hold the handgrip in the rest position, and an end-piece 13 forming part of the body and to which there is fastened, with snap-fitting means 14 that can be operated using a pivoting sleeve 15 the rear end of the elongate element C. A hairpin spring 10, in contact with the handgrip 6, roughly midway through its travel, forms a tactile threshold which alerts the operator to the fact that the needle is fully deployed, without ejecting a fastener. To complete the placement cycle as far as the ejection of a fastener, a greater force needs to be exerted on the handgrip 6. All the elements of the handgrip with the exception of the axles, the screws and the springs, are obtained by the moulding of plastic.

The handgrip 6 comprises a two-finger fork 6a which fingers are able to collaborate with studs 8a projecting laterally from the lever 8 to cause this lever to pivot forwards. The fingers 6a, the studs 8a and the lever 8 constitute the first controls of the appliance. The second controls consist of two cheeks 6b, which, at their front end, have a cam profile 6c visible in FIGS. 2 and 10.

Figure 6:
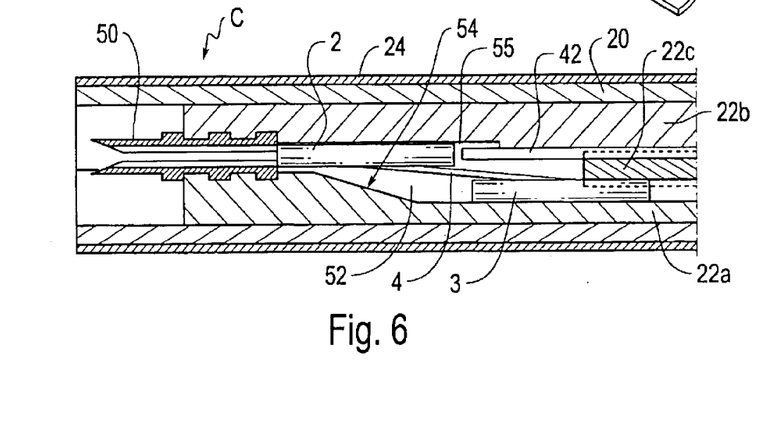
FIG. 6 is a part view in section on VI—VI of FIG. 5.

As shown in FIGS. 2 and 3, the elongate element C comprises a tubular body 20 in which there are slidably mounted a magazine slide 22 and a cage 23. The latter is connected, by a tubular metal portion 24, to a piston 25 entering the handgrip body and pressing against the cam profiles 6c. The tubular body 20 is itself made up of two semicylindrical plastic shells assembled along their diametral plane by welding or bonding, each of the shells itself being monolithic or made up of two elements assembled by nesting and riveting of their common ends. As this method of attachment is within the competence of the person skilled in the art, it is not deemed necessary to depict it in order not to overburden the drawings. As a preference and as shown in FIG. 6, the multi-part body 20 is arranged in a tubular metal band 21 extending right along its length and stiffening the elongate element C.

This method of construction and of connection makes it possible, within the tubular body 20, to produce various partitions or flanges, visible in FIG. 3, such as:

the flange 26 against which a spring 27 pushing the piston 25 against the cam profile 6c of the handgrip 6 bears, a partition 28 against which an arming sleeve 29, constantly subjected to the action of a spring 30 bearing against another flange 32 bears, a bearing 33 in which the flange of a holding sleeve 34 is trapped, a flange 35 against which the magazine slide 22 bears when it is in the rest position, and a partition 31 entering the cage 23 and against which its return spring 38 bears.

Passing axially through the piston 25 is a control rod 36 which also passes through the tube 24 connecting the piston with the cage 23 and which enters the cage where its front end receives, via a flange 37, the thrust of the spring 38. The rod 36 is extended by an axial rod 39, of smaller diameter than it and of which the front end 39a, bent and bent back again, is connected to the slide 22 as shown in FIG. 7.

The cage 23 which is mounted to slide in the tubular body 20 is extended forwards by a tubular end-piece 23a of a smaller diameter than it. The internal bore of this end-piece serves to guide a cylindrical shaft 40 through which the rod 39 passes axially and which is known as a hollow grooved shaft. Finally, the cage 23 is secured to the push rod 42 passing through the slide 22.

Figure 7:
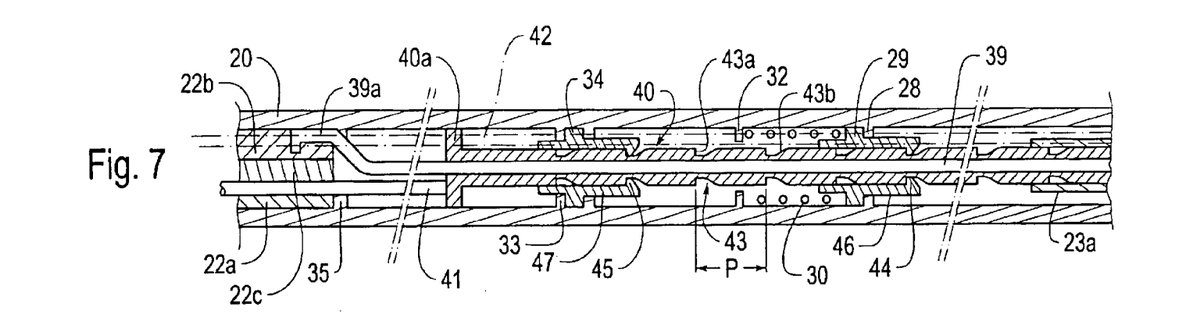
FIG. 7 is a part view in section, on an enlarged scale, on VII—VII of FIG. 3 when the appliance is at rest.
Figure 8:
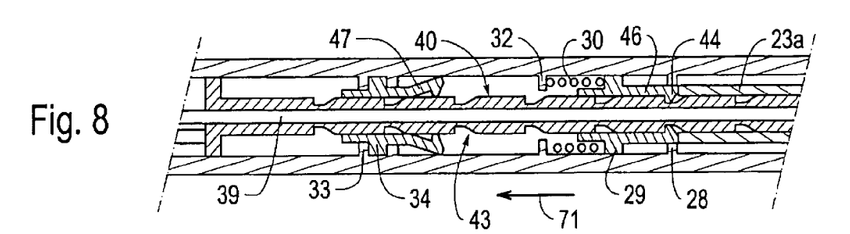
FIGS. 8 and 9 are views in section similar to FIG. 7, showing the grooved shaft in the phases of advancement by one step of the arming sleeve and of the grooved shaft and of return of this sleeve to the rest position, respectively.
Figure 9:
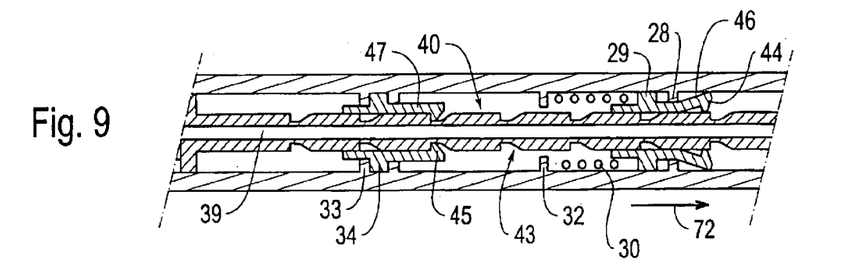

As shown in greater detail in FIGS. 7 to 9 which are views in section on a plane offset by 90° to the plane of section of FIG. 3, the shaft 40 extends beyond the bearing 33 for the holding sleeve 34 and has a piston-shaped end 40a which slides in the tubular body 20 and participates in its translational guidance. This end 40a is secured to a buffer rod 41 which extends longitudinally and enters the slide 22. The shaft 40 has external grooves 43. In each of these grooves, the front edge 43a is straight, that is to say lies in a diametral plane, while the rear edge 43b is sloped and diverges from the straight edge starting from the bottom of the groove. These grooves are distributed along the shaft 40 with a spacing P of a value equal to the length L (FIG. 1) of the catching bar 3 of a fastener A. They are intended to collaborate with the teeth 44 and 45 respectively of opposed elastic tabs 46, 47 respectively secured one to the arming sleeve 29 and the other to the holding sleeve 34.

Figure 4:
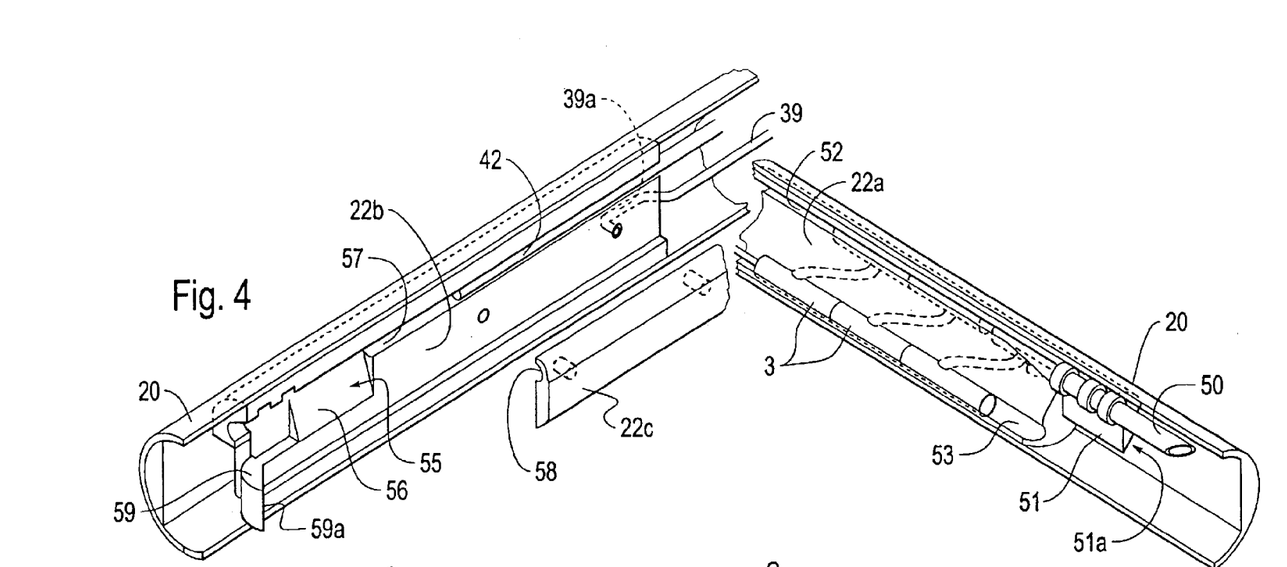
FIG. 4 is an exploded perspective view on an enlarged scale of the front end of the elongate element and of the magazine slide.
Figure 5:
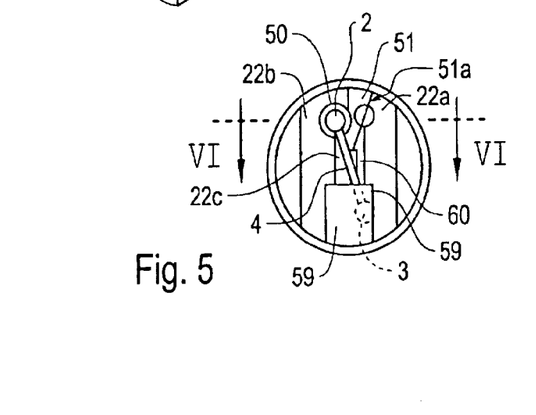
FIG. 5 is a front elevation on an enlarged scale of the front end of the elongate element.

As shown in greater detail in FIGS. 4 to 6, the magazine slide 22 is formed of two plastic shells 22a, 22b assembled, by bonding or welding, along their longitudinal and vertical mid-plane, enclosing an insert plate 22c.

The shell 22a is secured, at its end, to a hollow and split needle 50 and near its edges has two longitudinal slots, namely a slot 52 acting as housing for the anchoring bars 2 of the fasteners A, and a slot 53 acting as housing for the catching bars 3 of the same fasteners. These two slots are in one and the same vertical plane, separate from the one passing through the needle, and the one 53 opens freely from the front end of the shell 22a, while the one 52 dies out against an inclined plane 54, visible in FIG. 6. The latter encourages the anchoring bar 2 of the first fastener to move transversely until this bar comes behind and onto the longitudinal axis of the hollow needle 50, into an accommodating housing 55 as shown in FIG. 4.

The shell 22a further comprises, beside the needle 50, a rib 51 projecting downwards and having, above the path of the catching bar leaving the slot 53, a sloping face 51a.

FIG. 6, which depicts the appliance in the rest position, shows that, in this position, the rod of the plunger 42 is set back from the rear end of the needle 50 to uncover the accommodating housing 55 formed in the other shell 22b.

FIG. 4 shows that the accommodating housing 55 for the anchoring bar 2 of the first fastener is extended downwards by an inclined face 56 that supports the connecting strip 4 of the fastener. This shell 22b also has a semicylindrical slot 57 which, together with a complementary slot 58 formed in the plate 22c, forms a channel for guiding the plunger rod 42. This channel is coaxial with the needle 50. Via its rear part, this shell 22b is connected to the end 39a of the control rod 39, while its front end is equipped, in the part which lies under the needle, with a transverse finger 59 projecting towards the other shell, having a sloping face 59a and the benefit of which will be specified later on.

The insert plate 22c has a width allowing it to be inserted between the slots 52 and 53 of the shell 22a and a thickness allowing it to form, with this shell 22a, a passageway 60, visible in FIG. 5, leaving a space for the connecting strips 4 of the fasteners.

The magazine slide 22 thus formed has a length which allows it to store several fasteners A and, for example, ten fasteners.

When the appliance is at rest, the handgrip 6 is in the position depicted in FIG. 2, with the axial control rod 36 pressing against the lower end of the lever 8 and the piston 25 pressing against the ramps 6c of the handgrip 6. The magazine slide 22 is in a retracted position inside the tubular body 20. The needle 50 is retracted inside the body and the push rod 42 which uncovers the accommodating housing 55 is exerting no force on the anchoring bar 2 arranged this housing. Likewise, the catching bars 3 of the fasteners A in attendance in the magazine are in contact with one another, while the catching bar of the last fastener is near, with or without contact, the end of the buffer rod 35, but without significant force.

As a result, none of the fasteners is subjected to any force able, over time, to cause it to creep, to deform it and to disrupt its transfer.

Figure 11:
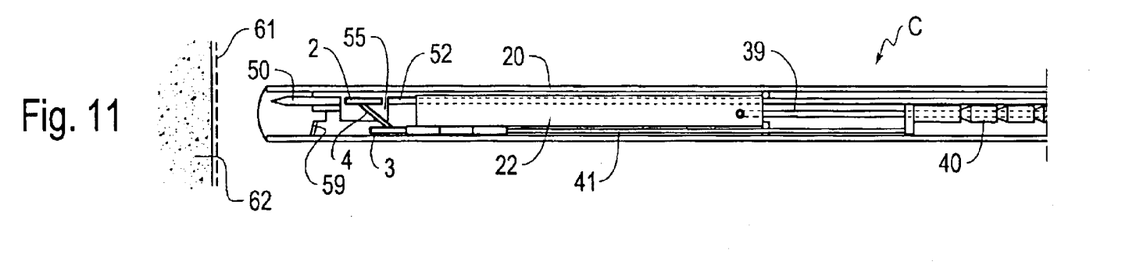
FIGS. 11 to 16 are views in longitudinal section of the elongate element and of its components when they are at rest, in the phase of leaving the needle, in the phase of starting and ending ejection, in the phase of withdrawal of the ejector, and in the phase of withdrawal of the slide, respectively.
Figure 12:
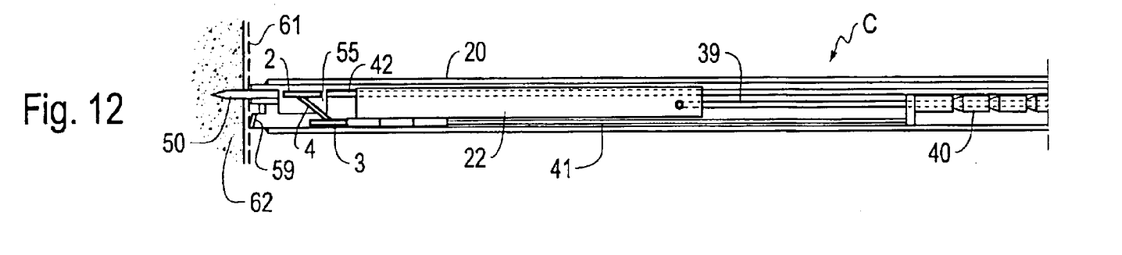

In use, the elongate element C of the appliance is introduced, with the needle 50 retracted, into a trocar. From there, it can be used in two ways:

engagement is performed until there is contact with the tissues, then the needle is deployed by actuating the handgrip 6, to pass through the tissues as shown in FIG. 12, engagement is performed stopping the end of the body 20 near but some distance from the wall that is to be reinforced, as shown in FIG. 11, then by commanding deployment of the needle without making it penetrate the tissues.

The latter solution is preferred because it allows the position of the needle 50 with respect to the regions that are to take a fastener to be seen and this position to be adapted by pivoting the element C with respect to the body for holding. It is therefore not until the needle 50 has been correctly positioned that it is introduced, by moving the appliance as a whole, into the two tissues 61, 62 that are to be connected, for example, a textile reinforcement 61 and an abdominal wall 62.

To deploy the needle 50, the operator presses the handgrip 6 so that it pivots, pushing it into the body. Over a first part of the travel the lower end of the lever 8 moves further than the piston 25 so that, via the rod 36, the slide 22 is moved, causing the needle 50 to project out from the body 20.

Figure 10:
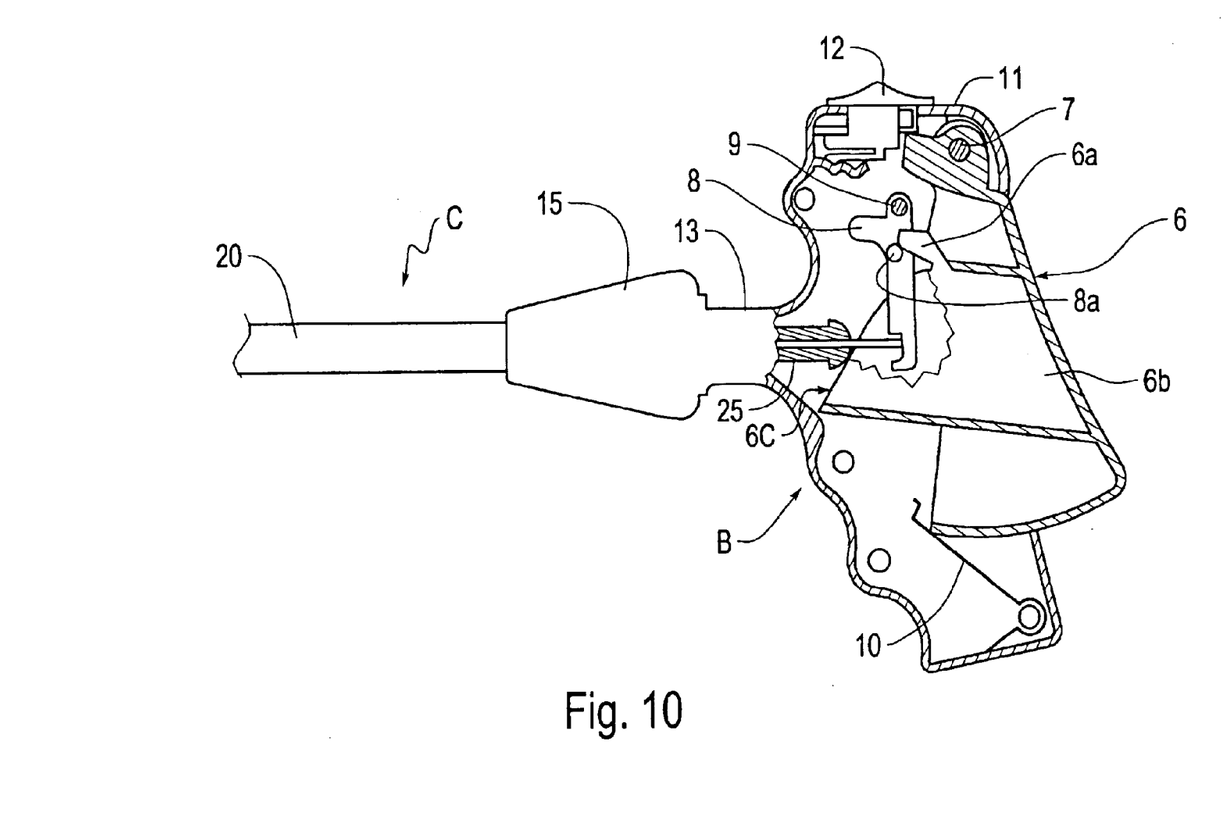
FIG. 10 is a part view in cross section of the handgrip, when it is being actuated.

FIG. 10 shows that, when the needle 50 is fully deployed, the handgrip reaches practically the middle of its travel and comes into contact with the hairpin spring 10. Because of the resistive force it applies on the handgrip 6, this spring indicates to the operator that this position has been reached and that continuing the movement may cause a fastener to be distributed. That makes it possible, while maintaining the force on the handgrip, for the element 20 to be pivoted if needed in order to suit the placement requirements. From this position on, the fingers 6a of the fork exert enough force on the studs 8a to hold the lever 8 in its position, but without causing it to move.

When the pivoting of the handgrip 6 is continued, it is the second controls which act and which cause only the piston 25 and therefore the plunger 42 to move, this movement being effected with respect to the magazine slide 22 which remains temporarily stationary.

Figure 13:
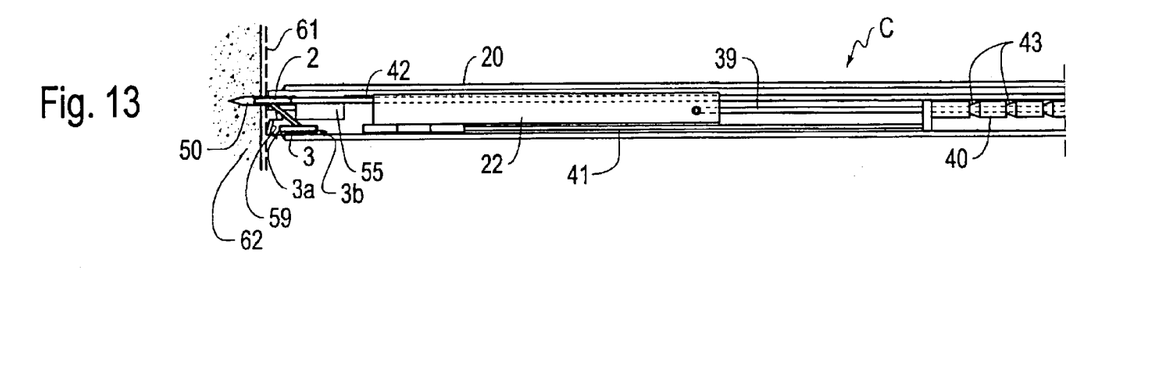

The push rod 42 is therefore moved longitudinally so that its end comes into contact with the rear part of the anchoring bar 2 of the fastener A arranged in the accommodating housing 5 and pushes this anchoring bar into the needle 50 as shown in FIG. 13.

The movement of the anchoring bar 2 pulls the connecting strip 4 and the catching bar 3 of the fastener that is in the process of being distributed. The downstream end 3a of the catching bar 3 comes into abutment against the finger 59 and this causes this bar to pivot upwards until it is standing up parallel to the reinforcement 61. During this movement, its upstream end 3b meets the sloping face 51a of the rib 51 which drives this end transversely so that once the bar has righted itself, this end no longer butts against the needle, but on the contrary moves away therefrom.

Figure 14:
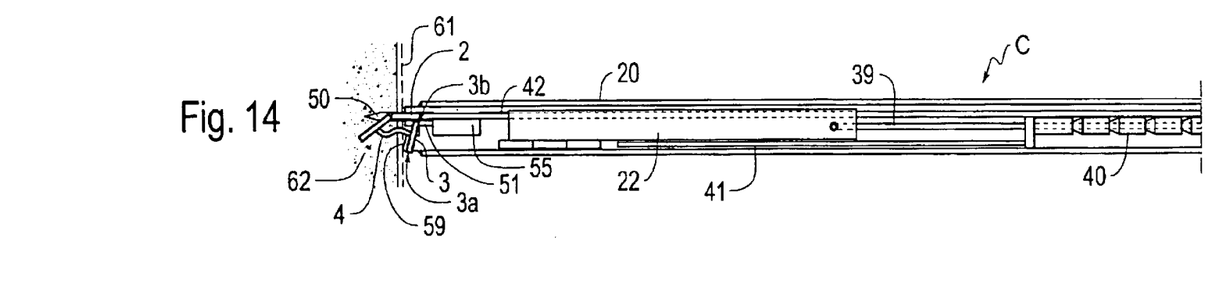

During this movement, the anchoring bar 2 advances along the needle. When the connecting strip 4 escapes this needle, the bar 2 can begin to pivot with the aid of the catching bar 3. What actually happens is that, via the connecting strip 4, the organized movement of the catching bar 3 has the effect of retaining the anchoring bar 2 which is thus forced to right itself and to anchor into the biological tissues 62 as shown in FIG. 14. During or at the end of the righting of the anchoring bar, the catching bar 3, which is more or less parallel to the textile reinforcement 61, slides, via its downstream end 3a, over the sloping face 59a of the finger 59 which drives it transversely and releases it.

Figure 15:
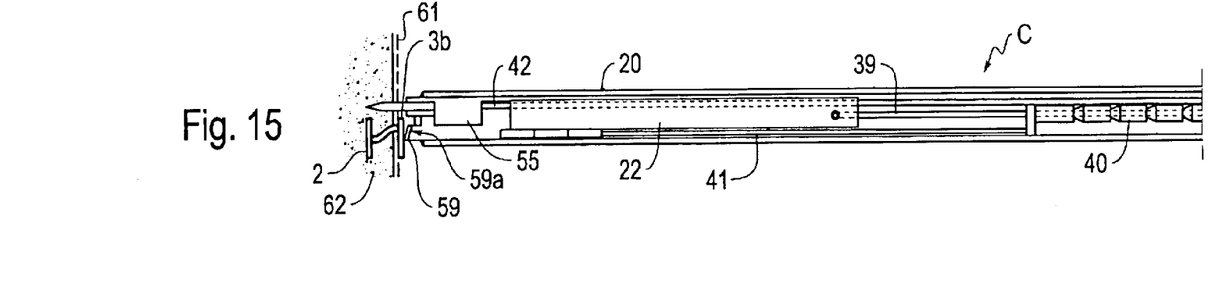
Figure 16:
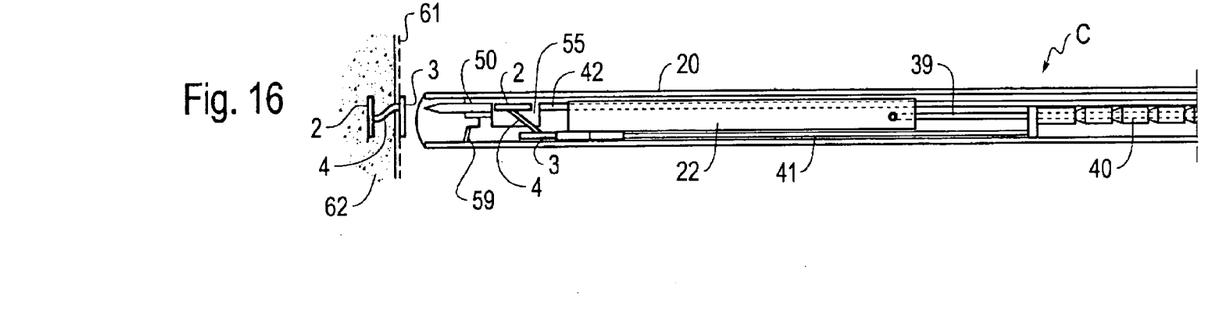

At the end of this movement and as shown in FIG. 15, the releasing of the action on the handgrip 6 allows the springs 27 and 38 to return the magazine slide 22 and the push rod 42, respectively. It is following this release of the handgrip that the appliance is extracted from the human body as shown in FIG. 16.

As can be seen from the foregoing, while the fastener A is being distributed, the distribution means employed allow its anchoring bar and its catching bar to right themselves to ensure perfect retention of these tissues.

It will be noted that, during the phase of distribution of the first fastener A, as shown in FIGS. 13 to 15, the accommodating housing 55 is closed off by the push rod 42 and that the awaiting fasteners maintain their position since, during this movement, they are not subjected to any force by the buffer bar 41. Indeed, the movement of the magazine slide 22 towards the front of the appliance carries with it the stock of fasteners and therefore moves them away from the free end of the buffer rod 41, which is not set into motion until the end of the movement of the push rod 42.

As shown in FIG. 8, this movement is afforded by contact of the end of the end-piece 23a of the cage 23 with the end of the tabs 46 of the arming sleeve 29. Because of the movement of this sleeve 29, the teeth of which remain engaged in a groove 43 of the shaft 40, this shaft is subjected to a longitudinal force which, via the sloping edges 43b of the groove engaged with the teeth 45 of the holding sleeve 34, causes the tabs 47 bearing these teeth 45 to part and allows this shaft to be moved longitudinally in the direction of the arrow 71 of FIG. 8. This movement is effected until the teeth 45 drop into the next groove 43 with the aid of the elastic return of the tabs 46. This position corresponds to the end of the movement of the cage 23 by the piston 25 resting against the cam profile 6c of the handgrip.

The result of all that is that the end of the buffer rod 41 has been advanced by one step by comparison with the initial position it occupied. In that way, as the magazine slide 22 retreats, the catching bar 3 of the last fastener comes into contact with the end of the buffer bar 41 and holds the row of fasteners, while the slide finishes its retraction into the body 20.

At the end of the retraction of the slide, the anchoring bar 22 of the first fastener comes into contact with the ramp 54, shown in FIG. 6, which ramp transfers it into the accommodating housing 55.

Because of the functional clearances in the appliance and because of the absence of spring means pushing the fasteners towards the exit from the magazine, the anchoring bar 2 of the first fastener is stored without stress in the accommodating housing 55 while its catching bar 3, whether or not it is resting against the catching bars of the other fasteners A stored, is under no stress or is subjected to a bearing force that is not high enough to deform it since, even if the catching bar 3 of the last fastener remains in contact with the buffer bar 41, it is without stress.

FIG. 9 shows that the release of the handgrip 6 causing the retreat of the slide into the tubular body 20 of the elongate element C moves the end-piece 23a of the arming sleeve 29 away and allows this sleeve, under the thrust of its spring 30, to move in the direction of the arrow 72, this being all the easier since, under the force to which it is subjected, its teeth 44 meeting the sloping face 43b of the groove 43 in which they lie, cause the tabs 46 to part until they drop back into the next groove, arming the device for a subsequent movement of the buffer rod.

The appliance which has been described in the context of its application to the storage, distribution and placement of surgical fasteners made of bioabsorbable low elasticity material may very well distribute fasteners made of a material having better mechanical properties since the storage, distribution and placement takes place under more disadvantageous conditions.

By way of example, for an appliance the outside diameter of the elongate element C of which is 10 millimetres, distributing couched I-shaped fasteners 7 millimetres tall and anchoring and catching bars 7 millimetres long, the travel of the magazine slide is of the order of 13 millimetres, while the travel of the ejection plunger 42 is of the order of 30 millimetres with the shaft 40 bearing the grooves 43 moving over the last 7 millimetres of the travel.

What is claimed is:

1. Appliance for storing, distributing and placing couched I-shaped surgical fasteners, comprising a handgrip body equipped with first controls and second controls on a handgrip and with an end-piece, and an elongate element, attached and fixed to the end-piece, wherein the elongate element is made up of a body of tubular overall shape, the elongate element containing:
   near a free end, a magazine slide itself containing couched I-shaped fasteners each having an anchoring bar, a catching bar and a connecting strip, the slide being movable in the elongate element by a longitudinal rod actuatable by the first controls on the handgrip and secured to a split and longitudinal hollow needle able to project from the elongate element, and
   wherein the tubular body includes therein a means for distributing the stored fasteners one by one, the distribution involving transferring of the anchoring bar of a first fastener into an accommodating housing arranged in an extension of the split and longitudinal hollow needle, and the tubular body further includes therein an ejection plunger movable by the second controls on the handgrip and which is arranged in line with the split and longitudinal hollow needle so as to push the anchoring bar of the first fastener thereinto, wherein the accommodating housing of the magazine slide contains, at rest, the anchoring bar of the first fastener awaiting placement, wherein the catching bar of the first fastener, arranged at the end of the magazine, is free of any thrusting force, wherein the magazine slide comprises:
      below the split and longitudinal hollow needle and in a path via which the catching bar leaves the magazine, a transverse finger, wherein when the fastener is distributed by movement of the anchoring bar by means of the plunger, the transverse finger has a downstream end of the catching bar bear against the transverse finger to force the catching bar to pivot by raising an upstream end of the catching bar,
      beside the split and longitudinal hollow needle, a downwardly projecting rib for guiding the pivoting and movement of the upstream end of the catching bar so that the catching bar does not butt against the split and longitudinal hollow needle,
      and, on the transverse finger, a sloping face driving the downstream end of the catching bar transversely away from the transverse finger.

2. Appliance for storing, distributing and placing fasteners according to claim 1, wherein at rest, the front end of the plunger is spaced away from the rear end of the split and longitudinal hollow needle to form the accommodating housing containing the anchoring bar of the first fastener.

3. Appliance for storing, distributing and placing fasteners according to claim 1, wherein the catching bar of the first fastener is, in the magazine, in contact with the catching bars of other fasteners stored, and the catching bar of the last fastener is in contact, but without significant force, with an end of a buffer rod movable step by step, the buffer rod being connected to means, at the end of the movement of distributing the first fastener into tissue, and through movement of the second controls, to move it by the length of one catching bar of one fastener so that, as the magazine slide returns to a starting and rest position in the tubular body, contact between the end of the buffer rod and the catching bar of the last fastener causes the row of fasteners to move within the magazine, and causes the anchoring bar of the first fastener to be transferred into the accommodating housing.

4. Appliance for storing, distributing and placing fasteners according to claim 3, wherein the buffer rod, mounted to slide in the body of the magazine slide, is connected by the end to a shaft, the shaft being:
   mounted to slide on an axial rod extending between the first controls on the handgrip and the slide to which the axial rod is secured,
   equipped with grooves, spaced at a spacing equal to the length of the catching bar of a fastener and each equipped with a straight front edge and a sloping rear edge,
   held in a work position by notched elastic tabs projecting from a holding sleeve connected to the tubular body and the notched elastic tabs having teeth of which enter one of the grooves arranged on the front part of the grooved shaft,
   connected to an arming sleeve arranged behind the holding sleeve which is mounted to slide in the tubular body against the action of return means pressing the arming sleeve against an internal flange of the tubular body, the connection between the grooved shaft and the arming sleeve being afforded by entrance of notched tabs secured to the arming sleeve in one of the grooves of the grooved shaft,
   and associated with movement means including a longitudinal body actuatable by the second controls and which, at the end of the travel for the distribution and placement of a fastener, pushes the arming sleeve by the length of a catching bar so as to move the grooved shaft, causing the tabs of the holding sleeve to part until the teeth enter the next groove, and causing the buffer rod to advance by the magnitude of the catching bar of a fastener.

5. Appliance for storing, distributing and placing fasteners according to claim 4, wherein the longitudinal body causing the arming sleeve to move includes a tubular end-piece surrounding the grooved shaft and projecting from a front end of a cage secured to the plunger, the cage containing the means for returning the axial rod of the slide being secured to a control piston entering the handgrip body and collaborating with the second controls.

6. Appliance for storing, distributing and placing fasteners according to claim 1, wherein a rear end of the rod connected to the magazine slide rests against a lever articulated in the handgrip body and able movable by a two-finger fork of the handgrip which is articulated in the handgrip body, while the piston secured to the cage and to the plunger rests against a cam profile formed on the handgrip body.

7. Appliance for storing, distributing and placing fasteners according to claim 1, wherein the magazine slide is formed of first and second plastic shells joined together along a median, longitudinal and vertical plane, the first shell secured to the split and longitudinal hollow needle having two longitudinal slots arranged near edges of the shell, one of the longitudinal slots receives the catching bars of the fasteners and the other longitudinal slot receives the anchoring bars, the slot for the catching bars opening freely at the front end of the slide while the slot for the anchoring bars opens onto an inclined plane for guidance in the direction of the split and longitudinal hollow needle, while the second shell has a longitudinal channel coaxial with the split and longitudinal hollow needle for the ejection plunger and, in the accommodating housing of the needle, a vertically inclined resting plane for the connecting strip of a fastener.

8. Appliance for storing, distributing and placing fasteners according to claim 7, wherein the longitudinal channel for the ejection plunger is formed of a first slot made in the corresponding second shell and of a second slot made in a plate attached inside the second shell, the plate having a width that allows the plate to be inserted between the two longitudinal slots made in the first shell for the anchoring bars and the catching bars respectively, and a thickness allowing the plate to delimit, with the first shell, a passageway for the passage of connecting strips of the fasteners.

9. Appliance for storing, distributing and placing fasteners according to claim 1, wherein the elongate element is made up of several plastic components assembled together and arranged in a tubular metal band.

\* \* \* \* \*